US012642957B2

(12) United States Patent
Wang et al.

(10) Patent No.: US 12,642,957 B2
(45) Date of Patent: Jun. 2, 2026

(54) H-BRIDGE CONTROL CIRCUIT FOR ELECTRO-STIMULATION THERAPEUTIC INSTRUMENT FOR NEUROMODULATION

(71) Applicants: Fasikl Incorporated, Dallas, TX (US); Hangzhou Fasikl Technology Co., Ltd, Hangzhou (CN)

(72) Inventors: Wei Wang, Hangzhou (CN); Baitong Wang, Hangzhou (CN); Jules Anh Tuan Nguyen, Dallas, TX (US); Bing Ye, Hangzhou (CN)

(73) Assignees: Fasikl Incorporated, Dallas, TX (US); Hangzhou Fasikl Technology Co., Ltd., Hangzhou (CN)

( * ) Notice: Subject to any disclaimer, the term of this patent is extended or adjusted under 35 U.S.C. 154(b) by 222 days.

(21) Appl. No.: 18/666,745

(22) Filed: May 16, 2024

(65) Prior Publication Data

US 2024/0299734 A1 Sep. 12, 2024

(51) Int. Cl.
*A61N 1/00* (2006.01)
*A61N 1/02* (2006.01)
*A61N 1/36* (2006.01)

(52) U.S. Cl.
CPC ......... *A61N 1/025* (2013.01); *A61N 1/36021* (2013.01)

(58) Field of Classification Search
CPC ............................ A61N 1/025; A61N 1/36021
See application file for complete search history.

(56) References Cited

U.S. PATENT DOCUMENTS

| | | | |
|---|---|---|---|
| 2010/0202172 A1 | 8/2010 | Skirda et al. | |
| 2011/0190849 A1* | 8/2011 | Faltys | A61N 1/37205 |
| | | | 607/50 |
| 2012/0116483 A1* | 5/2012 | Yonezawa | A61N 1/36 |
| | | | 607/2 |
| 2015/0097617 A1 | 4/2015 | Chak | |
| 2016/0367813 A1* | 12/2016 | Pepin | A61N 1/36125 |
| 2019/0229727 A1 | 7/2019 | Krishna | |

* cited by examiner

*Primary Examiner* — Unsu Jung
*Assistant Examiner* — James Moss
(74) *Attorney, Agent, or Firm* — Hemisphere Law, PLLC

(57) ABSTRACT

Disclosed is an H-bridge control circuit for an electro-stimulation therapeutic instrument for neuromodulation. The H-bridge control circuit includes an H-bridge circuit and a constant current source, where the H-bridge circuit includes a first positive channel metal oxide semiconductor (PMOS) transistor, a second PMOS transistor, a first negative channel metal oxide semiconductor (NMOS) transistor and a second NMOS transistor. Corresponding switching diodes are additionally arranged between the first PMOS transistor and a load and between the second PMOS transistor and the load to avoid an influence of safety of the therapeutic instrument by discharging charges during an interval of stimulation; and moreover, a resistance-capacitance (RC) circuit is additionally arranged between the first PMOS transistor, the second PMOS transistor and a control device such that connection and disconnection of the PMOS transistor can be controlled.

10 Claims, 3 Drawing Sheets

H-BRIDGE CONTROL CIRCUIT FOR ELECTRO-STIMULATION THERAPEUTIC INSTRUMENT FOR NEUROMODULATION

TECHNICAL FIELD

The present disclosure relates to an electro-stimulation therapeutic instrument for neuromodulation, and in particular to an H-bridge control circuit for an electro-stimulation therapeutic instrument for neuromodulation.

BACKGROUND

Transcutaneous electrical nerve stimulation belongs to peripheral nerve electro-stimulation therapy technology. With the advantages of non-trauma, non-invassiveness, easy operation, optimal tolerance, short duration of action, no side effects and low cost, the transcutaneous electrical nerve stimulation has become a characteristic of clinical application research and has been widely used, such as various nerve electro-stimulation therapeutic instruments generated based on the transcutaneous electrical nerve stimulation.

At present, most nerve electro-stimulation therapeutic instruments on the market mainly include a constant-voltage electro-stimulation therapeutic instrument and a constant-current electro-stimulation therapeutic instrument. The constant-voltage electro-stimulation therapeutic instrument refers to an instrument in which during electro-stimulation, a stimulation current is maintained unchanged and a stimulation voltage is adjusted along with a change in a load. On the contrary, the constant-current electro-stimulation therapeutic instrument refers to an instrument in which during electro-stimulation, a stimulation voltage is maintained unchanged and a stimulation current is adjusted along with a change in a load. Compared with the constant-voltage electro-stimulation therapeutic instrument, the constant-current electro-stimulation therapeutic instrument is often used in an accurate neuromodulation electro-stimulation therapy with strong stability, high accuracy, and optimal adaptability.

However, the current constant-current electro-stimulation therapeutic instrument, as shown in FIG. 1, generally uses a control mode of an H-bridge circuit and a constant current source. A high-voltage power supply and a constant current source are connected by means of the H-bridge circuit, and the H-bridge circuit is achieved through positive channel metal oxide semiconductor (PMOS) transistors and negative channel metal oxide semiconductor (NMOS) transistors. That is, the PMOS transistors Q11 and Q12 are connected between two ends of the load and the high-voltage power supply separately. The NMOS transistors Q13 and Q14 are connected between two ends of the load and the constant current source separately, and electrode plates are connected to the two ends of the load. By controlling connection and disconnection of the MOS transistors, forward and reverse bidirectional currents can be output on the load, thereby achieving neural electro-stimulation; moreover, a gate of the PMOS transistor Q11 is connected to a control signal by means of resistors R12 and R13, and a source of the PMOS transistor is connected between the resistors R12 and R13 by means of the resistor R11; and a gate of another PMOS transistor Q12 is connected to another control signal by means of resistors R15 and R16, and a source of the PMOS transistor is connected between the resistors R15 and R16 by means of a resistor R4. The control signal is a pulse width modulation (PWM) signal, is generally a low voltage output by a single chip microcomputer, and has an electrical level generally ranging from 3 V to 5 V. However, the high-voltage power supply has an electrical level generally ranging from 50 V to 100 V or even higher. Withstand voltages of the gate and the source of the PMOS transistor is generally below 20 V. Consequently, in order to protect the PMOS transistor from damage and to disconnect the PMOS transistor through a reasonable voltage, it is necessary to set a resistance value of the resistor R13 to be greater than that of the resistor R11, and a resistance value of the resistor R16 to be greater than that of the resistor R14. In this case, partial voltages of the resistors R11 and R14 are smaller, thereby ensuring that the PMOS transistor will not be damaged or breakdown. However, since the power supply is a high-voltage direct current supply, it is necessary to maintain the resistance values of the resistors R13 and R16 above 100 K. That is, transistors of the gates of the PMOS transistors Q11 and Q12 are extremely high. The connection and disconnection speed of the MOS transistor depends on charging and discharging time of a gate capacitance. When the transistor of the gate of the MOS transistor is high, the charging and discharging time of the gate capacitance of the MOS transistor will be delayed, thereby making the connection and disconnection speed of the MOS transistor extremely slow. Slowing down the connection and disconnection speed of the MOS transistor will delay rising edge time of a pulse current, making it difficult to accurately control a current pulse width, which will have an impact on fine neural stimulation therapy.

Furthermore, a human body is a capacitive load. After a round of stimulation, a large amount of charges will be accumulated at two ends of the load. During an interval of stimulation, the accumulated charges will be discharged through parasitic diodes of the two PMOS, resulting in a large pressure difference between the two ends of the load and an incapability of balancing the charges. Thus, a pressure difference on two sides of human muscle is equivalently large, which poses a safety hazard to the human body with long-term stimulation.

SUMMARY

In order to overcome the defects of the prior art, the objective of the present disclosure is to provide an H-bridge control circuit for an electro-stimulation therapeutic instrument for neuromodulation, which can solve the problem of potential safety hazards existing in an electro-stimulation therapeutic instrument for neuromodulation.

An objective of the present disclosure is achieved by using the following technical solution:

an H-bridge control circuit for an electro-stimulation therapeutic instrument for neuromodulation includes an H-bridge circuit and a constant current source, where the H-bridge circuit includes a first positive channel metal oxide semiconductor (PMOS) transistor, a second PMOS transistor, a first negative channel metal oxide semiconductor (NMOS) transistor and a second NMOS transistor, where a gate of the first PMOS transistor is connected to a first control signal, a source of the first PMOS transistor is connected to a power supply, and a drain of the first PMOS transistor is electrically connected to a first end of a load; a gate of the second PMOS transistor is connected to a second control signal, a source of the second PMOS transistor is connected to the power supply, and a drain of the second PMOS transistor is electrically connected to a second end of the load;

a gate of the first NMOS transistor is connected to a third control signal, a source of the first NMOS transistor is electrically connected to the first end of the load, and a drain of the first NMOS transistor is electrically connected to the constant current source; a gate of the second NMOS transistor is connected to a fourth control signal, a source of the second NMOS transistor is electrically connected to a second end of the load, and a drain of the second NMOS transistor is electrically connected to the constant current source of the electro-stimulation therapeutic instrument for neuromodulation;

a first switching diode is arranged between the drain of the first PMOS transistor and the first end of the load, an anode of the first switching diode is electrically connected to the drain of the first PMOS transistor, and a cathode of the first switching diode is electrically connected to the first end of the load; and a second switching diode is arranged between the drain of the second PMOS transistor and the second end of the load, an anode of the second switching diode is electrically connected to the drain of the second NMOS transistor, and a cathode of the second switching diode is electrically connected to the second end of the load; and the H-bridge control circuit further includes a first capacitor, a second capacitor, a first resistor and a second resistor, where one end of the first capacitor is connected to a first control signal, and the other end of the first capacitor is electrically connected to the gate of the first PMOS transistor; one end of the first resistor is electrically connected to the gate of the first PMOS transistor, and the other end of the first resistor is connected to the power supply; one end of the second capacitor is connected to the second control signal, and the other end of the second capacitor is electrically connected to the gate of the second PMOS transistor; and one end of the second resistor is electrically connected to the gate of the second PMOS transistor, and the other end of the second resistor is connected to the power supply.

Further, the H-bridge control circuit further includes a first voltage stabilizing diode and a second voltage stabilizing diode, where an anode of the first voltage stabilizing diode is electrically connected to the gate of the first PMOS transistor, and a cathode of the first voltage stabilizing diode is connected to the power supply; and an anode of the second voltage stabilizing diode is electrically connected to the gate of the second PMOS transistor, and a cathode of the second voltage stabilizing diode is connected to the power supply.

Further, the power supply is a high-voltage direct current.

Further, the H-bridge control circuit further includes: a power supply module configured to provide a power supply, where the source of the first PMOS transistor and the source of the second PMOS transistor are both electrically connected to the power supply module.

Further, the H-bridge control circuit further includes: a booster circuit, where the source of the first PMOS transistor and the source of the second PMOS transistor are both electrically connected to the power supply module by means of the booster circuit; and the booster circuit is configured to boost the power source provided by the power supply module to obtain the power supply.

Further, the power supply module is a lithium battery.

Further, the first control signal, the second control signal, the third control signal and the fourth control signal are provided by a main control microcontroller unit (MCU); one end of the first capacitor is electrically connected to a first output end of the main control MCU and is connected to the first control signal; one end of the second capacitor is electrically connected to a second output end of the main control MCU and is connected to the second control signal; the gate of the first NMOS transistor is electrically connected to a third output end of the main control MCU and is connected to the third control signal; and the gate of the second NMOS transistor is electrically connected to a fourth output end of the main control MCU and is connected to the fourth control signal.

Further, the main control MCU is a single chip microcomputer, and the first control signal, the second control signal, the third control signal and the fourth control signal are all pulse width modulation (PMW) signals.

Further, the H-bridge control circuit further includes: a current sampling circuit, where one end of the current sampling circuit is electrically connected to the constant current source, the other end of the current sampling circuit is electrically connected to the main control MCU, and the current sampling circuit is configured to collect an actual current value of the constant current source in real time and send the actual current value to the main control MCU, such that the main control MCU detects an abnormality of a current value according to the actual current value of the constant current source to determine whether the therapeutic instrument works normally.

Further, the main control MCU detecting an abnormality of a current value according to the actual current value of the constant current source to determine whether the therapeutic instrument works normally specifically includes: the main control MCU comparing the obtained actual current value of the constant current source with a current value of the constant current source flowing through the load to detect the abnormality; and cutting off the power supply of the H-bridge circuit when detecting the abnormality.

Compared with the prior art, the present disclosure has the beneficial effects:

according to the present disclosure, the H-bridge circuit for an electro-stimulation therapeutic instrument for neuromodulation is improved, that is, the switching diode is additionally arranged between the load and the PMOS transistor, such that the problem that voltages at two ends of the load are inconsistent since charges accumulated at the two ends of the load are discharged by means of a parasitic diode of the PMOS transistor during an interval of stimulation can be solved, thereby ensuring use safety of the therapeutic instrument. Moreover, a low voltage and a high voltage are isolated through the capacitor, such that voltage drop is generated between the gate and the source of the PMOS transistor to start an opening and closing function of the PMOS transistor at the low voltage. The present disclosure features convenient operation, accurate control, etc.

DETAILED DESCRIPTION OF THE EMBODIMENTS

The present disclosure will be further described below in combination with the accompanying drawings and the particular embodiments, and it should be noted that on the premise of no conflict, the examples or the technical features described below can be combined freely to form a new example.

The present disclosure solves the problems that a current pulse width cannot be accurately controlled and potential safety hazards exist in an existing constant current electro-stimulation therapeutic instrument through improvement on the basis of an implementation solution of the existing constant current electro-stimulation therapeutic instrument.

Figure 1:
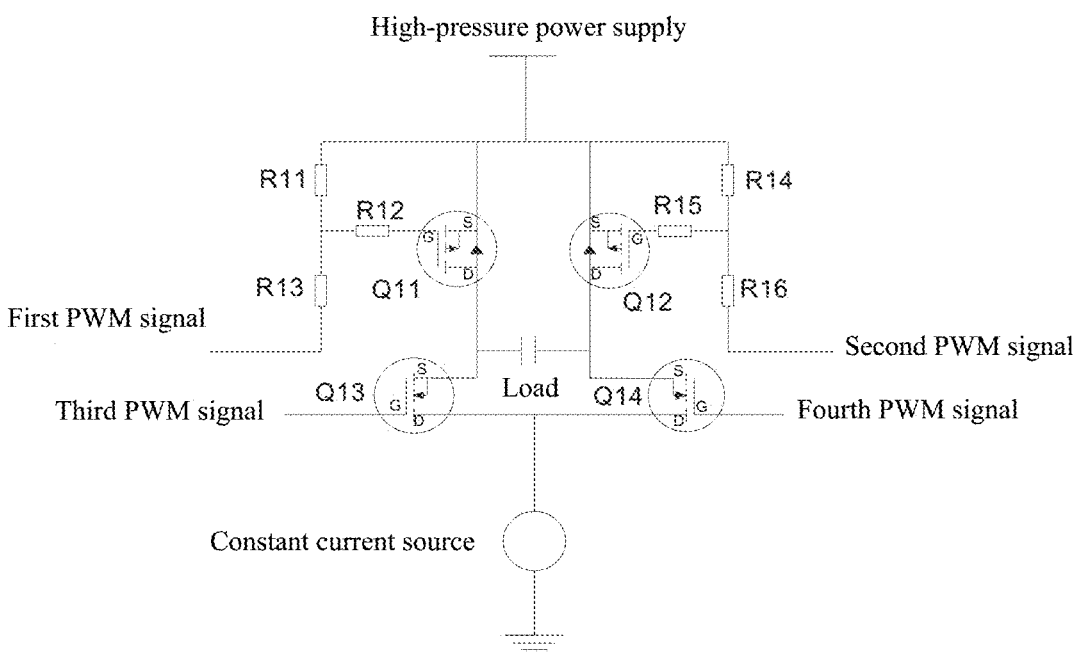
FIG. 1 is a circuit connection diagram of an H-bridge circuit, a constant current source and a load of an existing constant current electro-stimulation therapeutic instrument.
Figure 2:
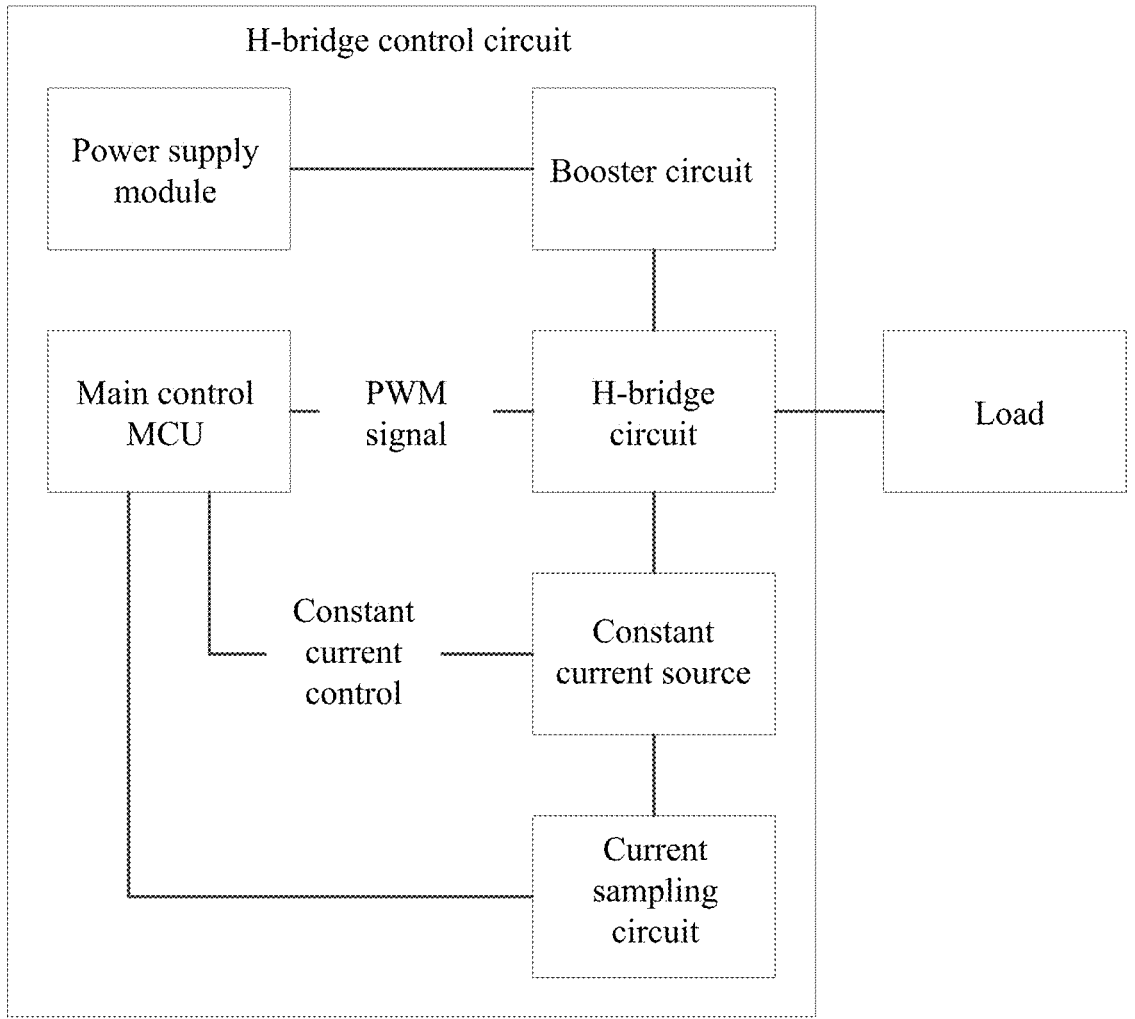
FIG. 2 is a schematic diagram of connection of an H-bridge circuit, a constant current source, a main control microcontroller unit (MCU) and a load in an H-bridge control circuit for an electro-stimulation therapeutic instrument for neuromodulation according to the present disclosure.
Figure 3:
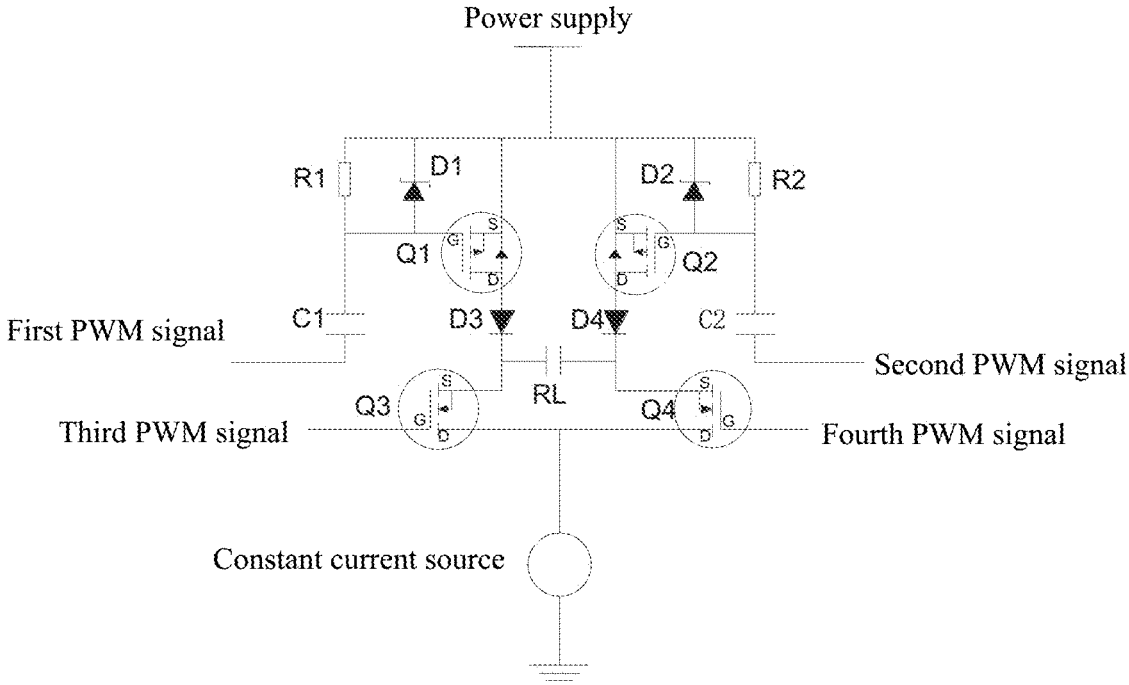
FIG. 3 is a circuit diagram of the H-bridge circuit in FIG. 2 and a circuit connection diagram of a constant current source and a load.

As shown in FIGS. 2 and 3, the present disclosure provides a preferred example. An H-bridge control circuit for an electro-stimulation therapeutic instrument for neuro-modulation includes an H-bridge circuit and a constant current source.

The H-bridge circuit includes a first positive channel metal oxide semiconductor (PMOS) transistor Q1, a second PMOS transistor Q2, a first negative channel metal oxide semiconductor (NMOS) transistor Q3 and a second NMOS transistor Q4.

The H-bridge circuit and the constant current source are electrically connected to the load RL. A magnitude and direction of a current output from the constant current source to the load RL are controlled by means of the H-bridge circuit. In fact, during use, the H-bridge circuit does not make direct contact with a human body portion, but an output end of the H-bridge circuit is connected to an electrode plate. The electrode plate makes contact with the human body portion to achieve the purpose of stimulating the human body portion. The example only illustrates that only an output end of the H-bridge circuit is connected to the load RL to output an electrical signal to the load RL.

Specifically, a gate G of the first PMOS transistor Q1 is connected to a first control signal, a source S of the first PMOS transistor Q1 is connected to a power supply, and a drain D of the first PMOS transistor Q1 is electrically connected to a first end of a load RL.

The first control signal refers to a control device of the electro-stimulation therapeutic instrument for neuromodulation, which generally uses a main control microcontroller unit (MCU). That is, the first control signal is input to the gate G of the first PMOS transistor Q1 by means of the main control MCU, such that a voltage drop is generated between the gate G and the source S of the first PMOS transistor Q1, and communication and cutoff of the first PMOS transistor Q1 are achieved. That is, opening and closing of the first PMOS transistor Q1 are controlled.

Similarly, a gate G of the second PMOS transistor Q2 is connected to a second control signal, a source S of the second PMOS transistor Q2 is connected to the power supply, and a drain D of the second PMOS transistor Q2 is electrically connected to a second end of the load RL. The second control signal is output to the gate G of the second PMOS transistor Q2 by means of the main control MCU, such that a voltage drop is generated between the gate G and the source S of the second PMOS transistor, and opening and closing of the second PMOS transistor Q2 are controlled.

A gate G of the first NMOS transistor Q3 is connected to a third control signal, a source S of the first NMOS transistor Q3 is electrically connected to the first end of the load, and a drain D of the first NMOS transistor Q3 is electrically connected to the constant current source. A gate G of the second NMOS transistor Q4 is connected to a fourth control signal, a source S of the second NMOS transistor Q4 is electrically connected to a second end of the load, and a drain D of the second NMOS transistor Q4 is electrically connected to the constant current source. That is, the third control signal is output to the first NMOS transistor Q3 by means of the main control MCU to control opening and closing of the third NMOS transistor Q3, and the fourth control signal is output to the second NMOS transistor Q4 by means of the main control MCU to control opening and closing of the fourth NMOS transistor Q4.

Preferably, the main control MCU in the example is usually a single chip microcomputer. The first control signal, the second control signal, the third control signal, and the fourth control signal are all pulse width modulation (PWM) signals. That is, the first control signal is a first PWM signal, the second control signal is a second PWM signal, the third control signal is a third PWM signal, and the fourth control signal is a fourth PWM signal. Specifically, the main control MCU is provided with a first output end, a second output end, a third output end and a fourth output end. The first control signal is output to the first PMOS transistor Q1 by means of the first output end, the second control signal is output to the second PMOS transistor Q2 by means of the second output end, the third control signal us output to the third PMOS transistor Q3 by means of the third output end, and the fourth control signal is output to the fourth PMOS transistor Q4 by means of the fourth output end.

A first switching diode D1 is arranged between the drain D of the first PMOS transistor Q1 and the first end of the load RL, an anode of the first switching diode D1 is electrically connected to the drain D of the first PMOS transistor Q1, and a cathode of the first switching diode is electrically connected to the first end of the load RL; and a second switching diode D2 is arranged between the drain D of the second PMOS transistor Q2 and the second end of the load RL, an anode of the second switching diode D2 is electrically connected to the drain D of the second NMOS transistor Q2, and a cathode of the second switching diode is electrically connected to the second end of the load RL.

According to the present disclosure, the first switching diode D1 is additionally arranged between the drain D of the first PMOS transistor Q1 and the load RL, and the second switching diode D2 is additionally arranged between the drain D of the second PMOS transistor Q2 and the load RL such that by means of the first switching diode D1 and the second switching diode D2, charges accumulated at two ends of the load RL cannot be discharged by means of parasitic diodes of the first PMOS transistor Q1 and the second PMOS transistor Q2 during an interval of stimulation of therapeutic pulse (in this case, all MOS transistors are in a closed state), thereby solving the problem of a voltage difference caused by inconsistent potentials at two ends of the load RL, and ensuring safety. That is, since a human body is a capacitive load, charges are accumulated at two ends of the capacitive load (i.e. at the two ends of the load RL) after a round of stimulation, and the accumulated charges are discharged to the corresponding sources S of the first PMOS transistor and the second PMOS transistor by means of the parasitic diodes of the first PMOS transistor Q1 and the second PMOS transistor Q2, resulting in a large voltage difference between two ends of the load RL, and an incapability of balancing the charges. A voltage difference between two sides of a muscle of the human body is equivalently large. Such long-term stimulation has potential safety hazards, which is not conducive to neurotherapy. Therefore, the switching diode is arranged between the capacitive load and the PMOS transistor in the present disclosure, such that discharge of the charges is avoided, charge balance is ensured, the voltage difference is avoided, and safe operation is ensured.

Preferably, the H-bridge control circuit further includes a first voltage stabilizing diode D1, a first capacitor C1 and a first resistor R1. One end of the first capacitor C1 is electrically connected to the first output end of the main control MCU, and the other end of the first capacitor is electrically connected to the gate G of the first PMOS transistor Q1. One end of the first resistor R1 is electrically connected to the gate G of the first PMOS transistor Q1, and the other end of the first resistor is connected to the power supply. An anode of the first voltage stabilizing diode D1 is connected to the power supply, and a cathode of the first voltage stabilizing diode is electrically connected to the gate G of the first PMOS transistor Q1.

Through the first voltage stabilizing diode D1, it can be ensured that the power supply of the gate G of the first PMOS transistor Q1 is stabilized at a maximum voltage value of the MOS transistor, so as to protect the MOS transistor from breakdown. That is, when the first PMOS transistor Q1 is not opened, a high-voltage direct current of the power supply enters the gate G of the first PMOS transistor Q1 by means of the first resistor R1; and moreover, the high-voltage direct current of the power supply is isolated from a low-voltage control end of the main control MCU by means of the first capacitor C1. Then, the main control MCU can change an electrical level of the first capacitor C1 by means of the first PWM signal, such that the electrical level of the gate G of the first PMOS transistor Q1 is changed. Since the voltage of the source S of the first PMOS transistor Q1 is unchanged, a voltage drop is formed between the gate G and the source S of the first PMOS transistor Q1. Once the voltage drop satisfies an opening voltage of the PMOS transistor, the first PMOS transistor Q1 is opened to achieve the opening and closing function of the PMOS transistor.

According to the present disclosure, a high voltage and a low voltage are isolated through the first capacitor C1, such that the voltage drop between the gate G and the source S of the PMOS transistor is controlled to achieve the opening and closing function of the MOS transistor, components are saved, and opening and closing time is short; and rising edge time of a pulse current is shortened, and a current pulse width can be adjusted more accurately to achieve accurate treatment. Moreover, by using the first voltage stabilizing diode D1, it can be ensured that the power supply of the gate G of the first PMOS transistor Q1 is stabilized at a maximum voltage value of the MOS transistor, thereby avoiding breakdown of the MOS transistor.

Similarly, the H-bridge control circuit further includes a second voltage stabilizing diode D2, a second capacitor C2, and a second resistor R2. One end of the second capacitor C2 is electrically connected to the second output end of the main control MCU, and the other end of the second capacitor is electrically connected to the gate G of the second PMOS transistor Q2. One end of the second resistor R2 is electrically connected to the gate G of the second PMOS transistor Q2, and the other end of the second resistor is connected to the power supply. An anode of the second voltage stabilizing diode D2 is connected to the power supply, and a cathode of the second voltage stabilizing diode is electrically connected to the gate G of the second PMOS transistor Q2.

Similarly, by means of the second voltage stabilizing diode D2, it can be ensured that the power supply of the gate G of the second PMOS transistor Q2 is stabilized at the maximum voltage value of the MOS transistor, so as to protect the MOS transistor from breakdown. That is, when the second PMOS transistor Q2 is not opened, a high-voltage direct current of the power supply enters the gate G of the second PMOS transistor Q2 by means of the second resistor R2; and moreover, the high-voltage direct current of the power supply is isolated from a low-voltage control end of the main control MCU by means of the second capacitor C2. Then, the main control MCU can change an electrical level of the second capacitor C2 by means of the second PWM signal, such that the electrical level of the gate G of the second PMOS transistor Q2 is changed. Since the voltage of the source S of the second PMOS transistor Q2 is unchanged, a voltage drop is formed between the gate G and the source S of the second PMOS transistor Q2. Once the voltage drop satisfies an opening voltage of the PMOS transistor, the second PMOS transistor Q2 is opened to achieve the opening and closing function of the PMOS transistor.

According to the present disclosure, a high voltage and a low voltage are isolated through the second capacitor C2, such that the voltage drop between the gate G and the source S of the PMOS transistor is controlled to achieve the opening and closing function of the MOS transistor, components are saved, and opening and closing time is short; and rising edge time of a pulse current is shortened, and a current pulse width can be adjusted more accurately to achieve accurate treatment. Moreover, by using the second voltage stabilizing diode D2, it can be ensured that the power supply of the gate G of the second PMOS transistor Q2 is stabilized at the maximum voltage value of the MOS transistor, thereby avoiding breakdown of the MOS transistor.

When the main control MCU controls the first PMOS transistor Q1 and the first NMOS transistor Q3 to be opened and the second PMOS transistor Q2 and the second NMOS transistor Q4 to be closed, a forward pulse current is output to the load RL; and conversely, when the main control MCU controls the second PMOS transistor Q2 and the second NMOS transistor Q4 to be disconnected and the first PMOS transistor Q1 and the first NMOS transistor Q3 to be closed, a reverse pulse current is output to the load RL. The first PMOS transistor Q1 and the second PMOS transistor Q2 are high-voltage PMOS transistors, and the first NMOS transistor Q3 and the second NMOS transistor Q4 are high-voltage NMOS transistors.

Preferably, the power supply of the present disclosure is a high-voltage direct current.

Preferably, the present disclosure further includes: a power supply module and a booster circuit. An output end of the power supply module is electrically connected to an input end of the booster circuit, and an output end of the booster circuit outputs the power supply. The booster circuit is configured to boost the power source provided by the power supply module to obtain the power supply, i.e. high-voltage direct current.

More preferably, the power supply module is a lithium battery. The lithium battery has a voltage of 3.7 V. The power source provided by the lithium battery may be converted into the high-voltage direct current by means of the booster circuit.

Further, the present disclosure further includes a current sampling circuit. One end of the current sampling circuit is electrically connected to the constant current source, and the other end of the current sampling circuit is electrically connected to the main control MCU. The current of the constant current source is collected by means of the current sampling circuit to sent collected current data to the main control MCU, such that the main control MCU determines whether the current of the constant current source is normal according to the collected current data.

The main control MCU controls the current of the constant current source by sending a control signal to the constant current source, and collects the actual current of the constant current source by means of the current sampling circuit to determine whether the actual current is consistent with a current output by actually controlling the constant current source, i.e., to determine whether the actual pulse current is the same as a current value output by a control end, thereby determining whether the electrode plate of the therapeutic instrument is worn correctly. Moreover, by means of real-time detection of the current of the constant current source, an abnormal state can be quickly identified, a path between the H-bridge circuit and the power supply can be cut off in time under abnormal conditions, and high-voltage stimulation can be cut off, such that closed-loop control of nerve stimulation is achieved to reduce potential safety hazards.

Furthermore, the present disclosure provides an example of an operation principle of the therapeutic instrument. Assuming that the power supply is 100 V, and the voltage of the drain D and the voltage of the source S of the first PMOS transistor Q1 are both 100 V, the main control MCU can reduce the voltage of the gate G of the first PMOS transistor from 100 V to 95 V by controlling the 5V first PWM signal, but the voltage of the source S of the first PMOS transistor Q1 is kept maintained at 100 V. That is, a voltage drop is generated between the gate G and the source S of the first PMOS transistor Q1. In this case, the first PMOS transistor Q1 is disconnected such that the purpose of quickly controlling the high-voltage PMOS transistor to be disconnected under the low voltage can be achieved. Furthermore, during actual use, the interval of stimulation can be adjusted and controlled by adjusting a resistance value of the first resistor R1 and a capacitance value of the first capacitor C1.

According to the present disclosure, breakdown of the PMOS transistor is avoided through the voltage stabilizing diode, the voltage drop between the source S and the gate G of the PMOS transistor is achieved through the capacitor, and the connection and disconnection function of the PMOS transistor is further achieved. According to the present disclosure, the PMOS transistor is quickly disconnected at the low voltage and connected at the high voltage, the cost of components can be saved through the design of the floating gate, and the rising edge time of the pulse current can be shortened. Thus, the pulse width of the current can be adjusted more accurately to achieve accurate treatment.

According to the present disclosure, the switching diode is additionally arranged between the capacitive load and the PMOS transistor, thereby avoiding charge discharge during the interval of stimulation, ensuring charge balance between the electrodes during the interval of stimulation, and eliminating potential safety hazards. By ensuring charge balance between the electrodes, potential safety hazards caused by charge imbalance can be avoided, thereby improving the effect and safety of treatment. Moreover, the present disclosure further detects the current output from the therapeutic instrument, so as to timely find an abnormality, and timely switches the power supply when the abnormality is found, so as to ensure safety and reliability of treatment.

The above embodiments are only preferred embodiments of the present disclosure and cannot be used to limit the scope of protection of the present disclosure. Any non-substantial changes or substitutions made by those skilled in the art on the basis of the present disclosure fall within the scope of protection of the present disclosure.

What is claimed is:

1. An H-bridge control circuit for an electro-stimulation therapeutic instrument for neuromodulation, comprising an H-bridge circuit and a constant current source, wherein the H-bridge circuit comprises a first positive channel metal oxide semiconductor (PMOS) transistor, a second PMOS transistor, a first negative channel metal oxide semiconductor (NMOS) transistor and a second NMOS transistor, wherein a gate of the first PMOS transistor is connected to a first control signal, a source of the first PMOS transistor is connected to a power supply, and a drain of the first PMOS transistor is electrically connected to a first end of a load; a gate of the second PMOS transistor is connected to a second control signal, a source of the second PMOS transistor is connected to the power supply, and a drain of the second PMOS transistor is electrically connected to a second end of the load;

a gate of the first NMOS transistor is connected to a third control signal, a source of the first NMOS transistor is electrically connected to the first end of the load, and a drain of the first NMOS transistor is electrically connected to the constant current source; a gate of the second NMOS transistor is connected to a fourth control signal, a source of the second NMOS transistor is electrically connected to a second end of the load, and a drain of the second NMOS transistor is electrically connected to the constant current source of the electro-stimulation therapeutic instrument for neuromodulation;

a first switching diode is arranged between the drain of the first PMOS transistor and the first end of the load, an anode of the first switching diode is electrically connected to the drain of the first PMOS transistor, and a cathode of the first switching diode is electrically connected to the first end of the load; and a second switching diode is arranged between the drain of the second PMOS transistor and the second end of the load, an anode of the second switching diode is electrically connected to the drain of the second NMOS transistor, and a cathode of the second switching diode is electrically connected to the second end of the load; and the H-bridge control circuit further comprises a first capacitor, a second capacitor, a first resistor and a second resistor, wherein one end of the first capacitor is connected to a first control signal, and the other end of the first capacitor is electrically connected to the gate of the first PMOS transistor; one end of the first resistor is electrically connected to the gate of the first PMOS transistor, and the other end of the first resistor is connected to the power supply; one end of the second capacitor is connected to the second control signal, and the other end of the second capacitor is electrically connected to the gate of the second PMOS transistor; and one end of the second resistor is electrically connected to the gate of the second PMOS transistor, and the other end of the second resistor is connected to the power supply.

2. The H-bridge control circuit for an electro-stimulation therapeutic instrument for neuromodulation according to claim 1, further comprising: a first voltage stabilizing diode and a second voltage stabilizing diode, wherein an anode of the first voltage stabilizing diode is electrically connected to the gate of the first PMOS transistor, and a cathode of the first voltage stabilizing diode is connected to the power supply; and an anode of the second voltage stabilizing diode is electrically connected to the gate of the second PMOS transistor, and a cathode of the second voltage stabilizing diode is connected to the power supply.

3. The H-bridge control circuit for an electro-stimulation therapeutic instrument for neuromodulation according to claim 1, wherein the power supply is a high-voltage direct current.

4. The H-bridge control circuit for an electro-stimulation therapeutic instrument for neuromodulation according to claim 1, further comprising: a power supply module configured to provide a power source, wherein the source of the first PMOS transistor and the source of the second PMOS transistor are both electrically connected to the power supply module.

5. The H-bridge control circuit for an electro-stimulation therapeutic instrument for neuromodulation according to claim 4, further comprising: a booster circuit, wherein the source of the first PMOS transistor and the source of the second PMOS transistor are both electrically connected to the power supply module by means of the booster circuit; and the booster circuit is configured to boost the power source provided by the power supply module to obtain the power supply.

6. The H-bridge control circuit for an electro-stimulation therapeutic instrument for neuromodulation according to claim 5, wherein the power supply module is a lithium battery.

7. The H-bridge control circuit for an electro-stimulation therapeutic instrument for neuromodulation according to claim 1, wherein the first control signal, the second control signal, the third control signal and the fourth control signal are provided by a main control microcontroller unit (MCU);

one end of the first capacitor is electrically connected to a first output end of the main control MCU and is connected to the first control signal; one end of the second capacitor is electrically connected to a second output end of the main control MCU and is connected to the second control signal; the gate of the first NMOS transistor is electrically connected to a third output end of the main control MCU and is connected to the third control signal; and the gate of the second NMOS transistor is electrically connected to a fourth output end of the main control MCU and is connected to the fourth control signal.

8. The H-bridge control circuit for an electro-stimulation therapeutic instrument for neuromodulation according to claim 7, wherein the main control MCU is a single chip microcomputer, and the first control signal, the second control signal, the third control signal and the fourth control signal are all pulse width modulation (PMW) signals.

9. The H-bridge control circuit for an electro-stimulation therapeutic instrument for neuromodulation according to claim 7, further comprising: a current sampling circuit, wherein one end of the current sampling circuit is electrically connected to the constant current source, the other end of the current sampling circuit is electrically connected to the main control MCU, and the current sampling circuit is configured to collect an actual current value of the constant current source in real time and send the actual current value to the main control MCU, such that the main control MCU detects an abnormality of a current value according to the actual current value of the constant current source to determine whether the therapeutic instrument works normally.

10. The H-bridge control circuit for an electro-stimulation therapeutic instrument for neuromodulation according to claim 9, wherein the main control MCU detecting an abnormality of a current value according to the actual current value of the constant current source to determine whether the therapeutic instrument works normally specifically comprises: the main control MCU comparing the obtained actual current value of the constant current source with a current value of the constant current source flowing through the load to detect the abnormality; and cutting off the power supply of the H-bridge circuit when detecting the abnormality.

* * * * *